(12) United States Patent
Demos

(10) Patent No.: US 12,426,833 B2
(45) Date of Patent: *Sep. 30, 2025

(54) IMAGING SYSTEM AND METHOD FOR ENHANCED VISUALIZATION OF NEAR SURFACE VASCULAR STRUCTURES

(71) Applicant: Lawrence Livermore National Security, LLC, Livermore, CA (US)

(72) Inventor: Stavros Demos, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 321 days.

This patent is subject to a terminal disclaimer.

(21) Appl. No.: 17/154,710

(22) Filed: Jan. 21, 2021

(65) Prior Publication Data
US 2021/0169405 A1 Jun. 10, 2021

Related U.S. Application Data

(62) Division of application No. 14/897,042, filed as application No. PCT/US2014/041271 on Jun. 6, 2014, now Pat. No. 10,939,869.
(Continued)

(51) Int. Cl.
*A61B 5/00* (2006.01)
*A61B 5/02* (2006.01)

(52) U.S. Cl.
CPC .......... *A61B 5/489* (2013.01); *A61B 5/0059* (2013.01); *A61B 5/0075* (2013.01);
(Continued)

(58) Field of Classification Search
None
See application file for complete search history.

(56) References Cited

U.S. PATENT DOCUMENTS 5,847,394 A 12/1998 Alfano et al.
5,929,443 A 7/1999 Alfano et al.
(Continued)

FOREIGN PATENT DOCUMENTS

JP 2012164357 A 8/2012

OTHER PUBLICATIONS

S.G. Demos and R. R. Alfano, "Optical Polarization Imaging" Applied Optics, 36, 150-155, 1997.
(Continued)

*Primary Examiner* — Shahdeep Mohammed
(74) *Attorney, Agent, or Firm* — HARNESS, DICKEY & PIERCE, P.L.C.

(57) ABSTRACT

The present disclosure relates to a method for visualizing a sub-dermal structure. The method involves illuminating an imaged area of interest (AOI) including sub-dermal regions thereof with near-infrared (NIR) light. The NIR light is passed through a first optical system for controlling at least one of spectral and polarization properties thereof prior to illuminating the imaged AOI. One or more desired optical components of an optical signal reflected back from the imaged area of interest is detected, which represent specific portions of the sub-dermal regions where specific anatomical structure of interest is present. The desired optical components represent a vein visualization signal representing only a portion of the reflected optical signal that falls within a sub-range of intensities, relative to intensities of a remainder of the reflected optical signal. The sub-range of intensities assist in visualizing a vascular structure below a skin layer of a patient. The vein visualization signal may be used to generate a display of the vascular structure on a display system.

18 Claims, 8 Drawing Sheets

Related U.S. Application Data

(60) Provisional application No. 61/836,618, filed on Jun. 18, 2013.

(52) U.S. Cl.
CPC .......... *A61B 5/0077* (2013.01); *A61B 5/7203* (2013.01); *A61B 5/742* (2013.01); *A61B 5/02007* (2013.01); *A61B 2562/0233* (2013.01)

(56) References Cited

U.S. PATENT DOCUMENTS

| | | | |
|---|---|---|---|
| 6,032,070 | A | 2/2000 | Flock et al. |
| 6,353,226 | B1 | 3/2002 | Khalil et al. |
| 7,289,211 | B1 | 10/2007 | Walsh, Jr. et al. |
| 2002/0016533 | A1 | 2/2002 | Marchitto et al. |
| 2002/0058874 | A1 | 5/2002 | Ono et al. |
| 2006/0129037 | A1* | 6/2006 | Kaufman ............... A61B 5/489 600/322 |
| 2007/0161906 | A1 | 7/2007 | Zeman et al. |
| 2008/0004525 | A1 | 1/2008 | Goldman et al. |
| 2008/0027317 | A1 | 1/2008 | Wood et al. |
| 2008/0049982 | A1 | 2/2008 | Nagasaka et al. |
| 2008/0076983 | A1 | 3/2008 | Debreczeny et al. |
| 2009/0118623 | A1 | 5/2009 | Serov et al. |
| 2009/0245601 | A1* | 10/2009 | Cohen .................. A61B 5/0059 382/128 |
| 2011/0004106 | A1 | 1/2011 | Iwamiya et al. |
| 2012/0071765 | A1* | 3/2012 | Chinnock .............. A61B 5/489 600/476 |
| 2013/0324866 | A1* | 12/2013 | Gladshtein ........... A61B 5/0535 600/507 |
| 2014/0236019 | A1 | 8/2014 | Rahum |
| 2014/0350408 | A1* | 11/2014 | Goldman ............. A61B 5/0064 600/407 |

OTHER PUBLICATIONS

International Search Report and Written Opinion for PCT/US2014/041271, mailed Oct. 1, 2014; ISA/KR.

* cited by examiner

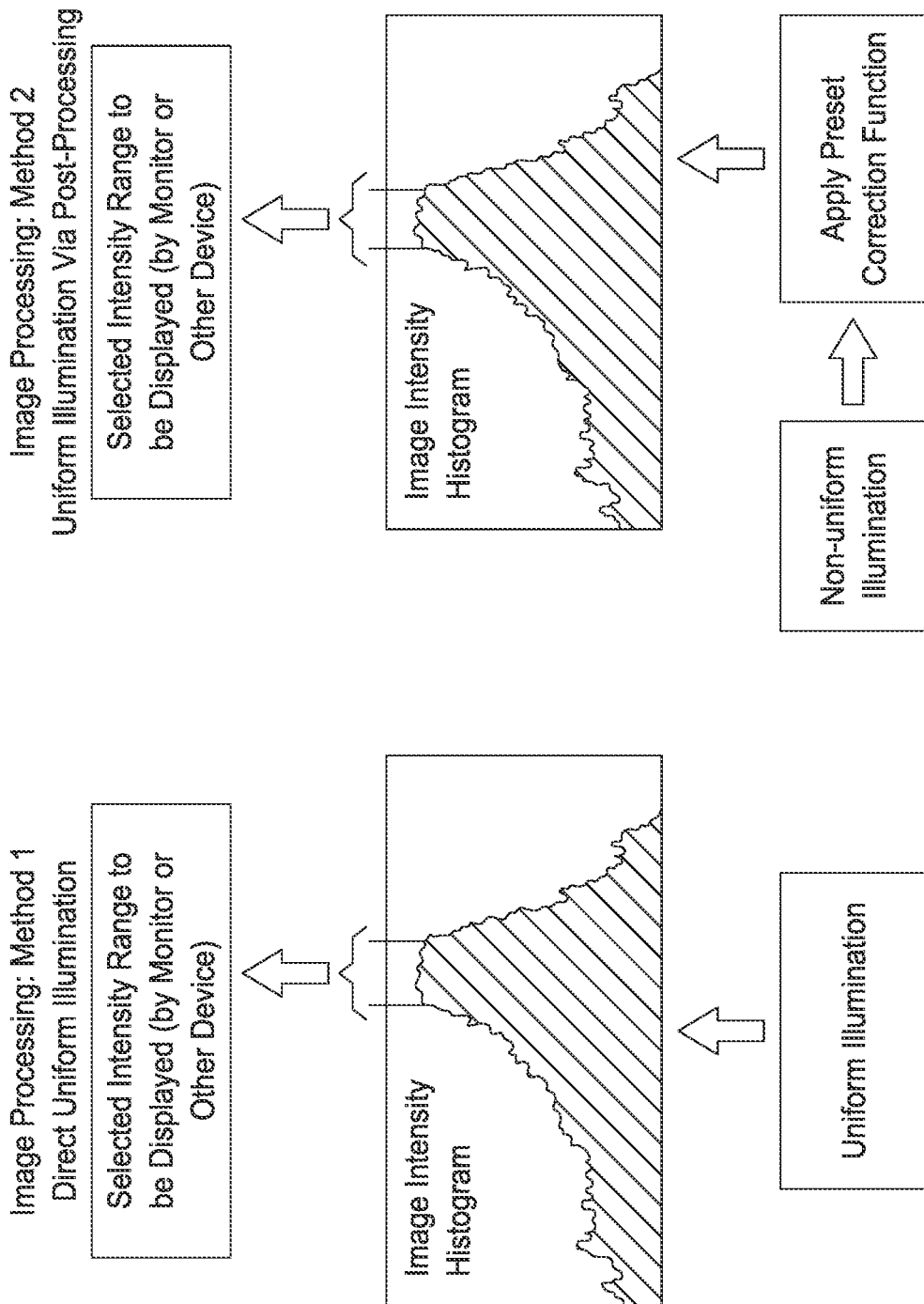

IMAGING SYSTEM AND METHOD FOR ENHANCED VISUALIZATION OF NEAR SURFACE VASCULAR STRUCTURES

CROSS-REFERENCE TO RELATED APPLICATIONS

This application is a divisional and claims priority from U.S. patent application Ser. No. 14/897,042, filed Dec. 9, 2015, which is a U.S. National Stage of International Application No. PCT/US2014/041271, filed Jun. 6, 2014; which claims priority to U.S. Patent Application No. 61/836,618, filed Jun. 18, 2013. The disclosure of each of the foregoing applications are incorporated herein by reference in its entirety.

FEDERALLY SPONSORED RESEARCH OR DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND OF THE INVENTION

Field of the Invention

The present application relates to imaging systems and methods, and more particularly to a sub-dermal visualization and imaging system and method using near infrared (NIR) light for enhanced imaging of veins and other near surface vascular structures.

Discussion of the Related Art

A common problem associated with the insertion of hypodermic needles and other devices in near surface veins of a patient is the inability to see or otherwise locate the vein to successfully insert the needle or device into the vein. The difficulty in visually locating vascular structures with the naked eye is mainly because the ability of visible photons to penetrate the tissue is very limited.

Vein visualization is currently commonly performed via a naked eye evaluation using mainly two markers. The first is based on the anatomical information as the veins often create a protrusion (especially the larger veins) that are located very close to the surface of the skin. The second is based on the higher penetration of the red components of the visible spectrum into the tissue. The red light encountering the veins is strongly absorbed by the blood and as a result, this location has the appearance of a dark blue-gray color that we are all familiar with. However, in people with higher melanin content in their skin, the red component is absorbed by the melanin making visualization of the veins even harder. In addition, more obese people tend to have more fat layers between the skin and the veins and the veins are located deep enough under the skin to be invisible by the naked eye. The interplay between light absorption and light scattering ultimately determines if a vein is visible by the naked eye.

There is therefore a need for an imaging system and method capable of enhanced visualization of sub-dermal structures such as veins and other near surface vascular structures. The present application thus addresses such a need.

SUMMARY

This section provides a general summary of the disclosure, and is not a comprehensive disclosure of its full scope or all of its features.

In one aspect the present disclosure relates to a method for visualizing a sub-dermal structure. The method comprises illuminating an imaged area of interest (AOI) including sub-dermal regions thereof with near-infrared (NIR) light. The NIR light is passed through a first optical system for controlling at least one of spectral and polarization properties of the NIR light prior to illuminating the imaged area of interest. The method further includes detecting one or more desired optical components of an optical signal reflected back from the imaged area of interest, wherein the one or more optical components represent specific portions of the sub-dermal regions where specific anatomical structure of interest is present. The one or more desired optical components of the detected optical signal comprise a vein visualization signal representing only a portion of the reflected optical signal that fall within a sub-range of intensities, relative to intensities of a remainder of the reflected optical signal. The sub-range of intensities assist in visualizing a vascular structure below a skin layer of a patient. The method further includes displaying the vein visualization signal to generate a display of the vascular structure on a display system.

In another aspect the present disclosure relates to a method for visualizing a sub-dermal structure. The method may comprise illuminating an imaged area of interest (AOI) including sub-dermal regions thereof with near-infrared (NIR) light. The NIR light is passed through a first optical system for controlling at least one of spectral and polarization properties of the NIR light prior to illuminating the imaged area of interest. The method further includes detecting one or more desired optical components of an optical signal reflected back from the imaged area of interest which have one or more desired spectral or polarization properties, wherein the one or more optical components represent specific portions of the sub-dermal regions where specific anatomical structure of interest is present, and where the imaged area of interest (AOI) is substantially larger than the sub-dermal regions having the specific anatomical of interest. The method further includes using the detected one or more desired optical components to produce an image intensity histogram, and analyzing the image intensity histogram and selecting therefrom only a selected sub-range of intensities forming a subportion of the detected one or more desired optical components. The selected sub-range of intensities comprise a vein visualization signal which assists in visualizing a vascular structure below a skin layer of a patient. The method further includes using the vein visualization signal to generate a display of the vascular structure on a display system.

In still another aspect the present disclosure relates to a method for visualizing a sub-dermal structure. The method may comprise illuminating an imaged area of interest (AOI) including sub-dermal regions thereof with near-infrared (NIR) light. The method further includes controlling spectral and polarization properties of the NIR light prior to the NIR light illuminating the imaged area of interest, and then using an optical Figure to rejection unwanted one or more components of an optical signal reflected back from the imaged area of interest, while passing a part of the optical signal being reflected back which has one or more desired spectral and polarization properties. The method further includes detecting one or more desired optical components of an optical signal reflected back from the imaged area of interest, wherein the one or more optical components represent specific portions of the sub-dermal regions where specific anatomical structure of interest is present. The method may further include creating a histogram using the one or more desired optical components, and using an image enhancing subsystem to analyze the histogram and to select therefrom only a sub-range of intensities present in the histogram. The sub-range of intensities represents a vein visualization signal, and the vein visualization signal representing the specific anatomical structure of interest. The method may further include displaying the vein visualization signal on a display system as an image in accordance with at least one of a selected aspect ratio, a desired resolution and an image contrast that enhances the image.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

FIG. 2 is an illustration of one example of a method in accordance with the present invention of image processing using direct uniform illumination of an area of interest.

FIG. 3 is an illustration of another example of a method in accordance with the present invention in which uniform illumination is achieved via post-processing of the detected optical signals.

DETAILED DESCRIPTION

Figure 1:
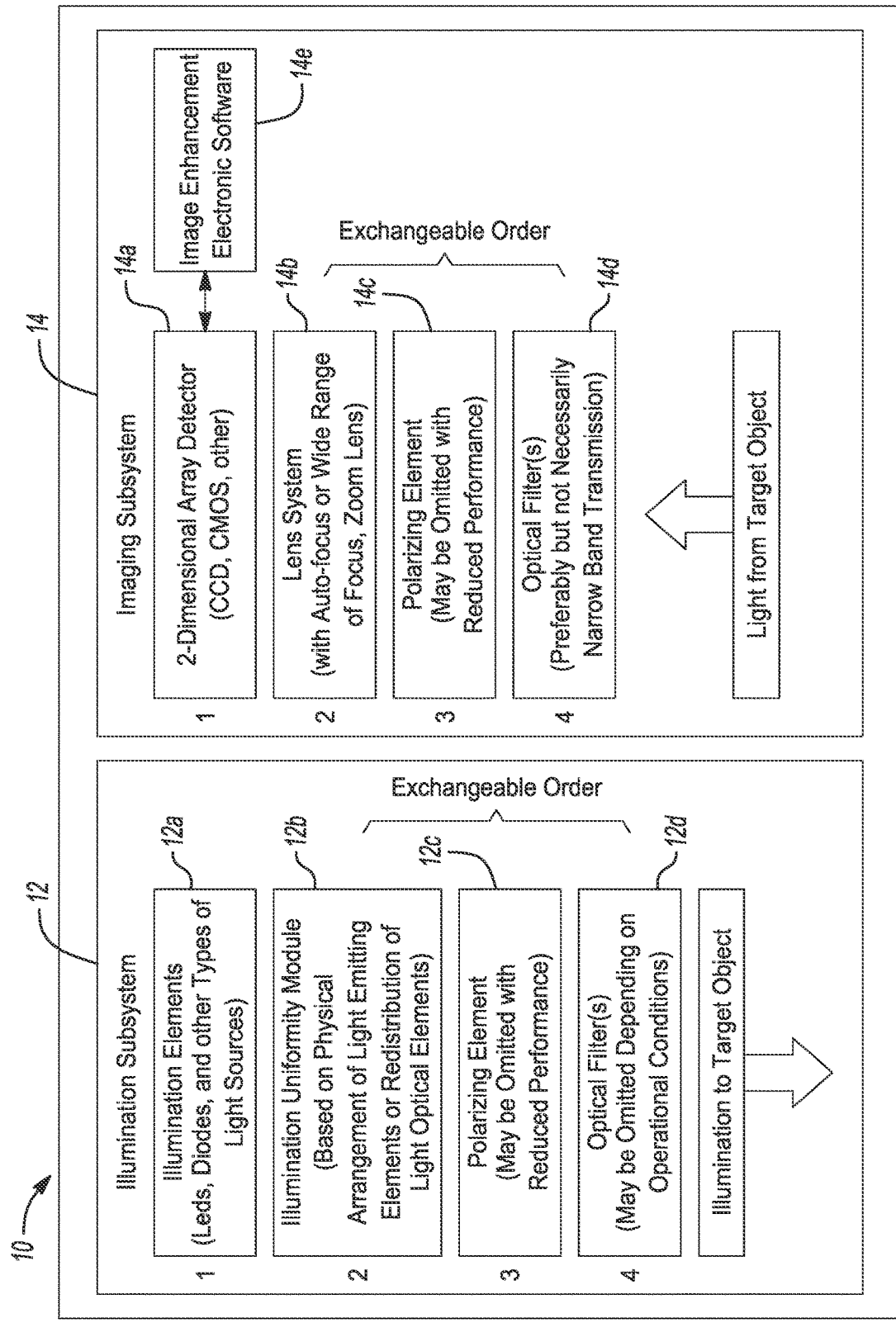
FIG. 1 illustrates a high level block diagram of one example embodiment of the present disclosure.

In the description of the invention herein, it is understood that a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Moreover, it is to be appreciated that the Figures, as shown herein, are not necessarily drawn to scale, wherein some of the elements may be drawn merely for clarity of the invention. Also, reference numerals may be repeated among the various Figures to show corresponding or analogous elements. Additionally, it will be understood that any list of such candidates or alternatives is merely illustrative, not limiting, unless implicitly or explicitly understood or stated otherwise. In addition, unless otherwise indicated, numbers expressing quantities of ingredients, constituents, reaction conditions and so forth used in the specification and claims are to be understood as being modified by the term "about."

Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

General Description

Near infrared (NIR) light is known to offer maximum penetration depth in tissues to improve visibility of the near surface vascular system. This is mainly due to the reduced absorption of blood and myoglobin. Blood and myoglobin limit the photon penetration depth at shorter wavelengths. Water limits the photon penetration depth at longer wavelengths. The reduced absorption of blood and water enables NIR light to reach and interact with the subsurface veins to bring image information back to be detected by an imaging device. However, although the absorption coefficient of blood in the NIR is reduced, blood still remains the main absorbing chromophore, thus causing the veins to appear as darker features independently of the illumination wavelength. In addition, better visualization of the veins using NIR illumination is attained by the reduced absorption by melanin and the reduced scattering of photons as a function of wavelength.

The problem of visualizing the subsurface vascular system, even with NIR light, arises from the fact that still only a portion of the light injected though the surface is able to reach the vein before being backscattered to reach the imaging device. Specifically, upon the illumination of the tissue with NIR light, a portion of the light will be reflected at the interface between tissue and air due to the change in the index of refraction. The resulting image component (specular reflection image) has no information on the spatial characteristics of the vein since it never interacted with it (i.e., propagated through the vein). The complementary image component contains photons that reached an adequate depth to interact with the vein, thus bearing information about its presence and geometrical characteristics when they are recorded by the imaging device. This small component of detected light is the Vein Visualization Signal (VVS) light. The ratio of the VVS to the total detected signal is continuously decreased as the vein is located deeper below the surface. Visualization of the vascular structure requires a contrast in the recorded image, which is typically presented with the vein having a darker appearance compared to the surrounding field.

Specific Description

Turning now to the drawings, the various embodiments of the present invention are directed to an imaging system 10, as shown generally by the block diagrams in FIG. 1, and a method in accordance therewith. In particular, FIG. 1 thus shows system 10 configured with an illumination subsystem 12 which illuminates a target object (as denoted with a large directional arrow) and on return, an imaging subsystem 14 which receives light from the target object (as also denoted with a large directional arrow). Illumination subsystem 12 thus shows example components and/or arrangements of components (denoted as 1, 2, 3, 4), but is not limited only to such disclosed example components and/or arrangements of components. In one example the illumination subsystem 12 may include illumination elements 12a, an illumination uniformity module 12b, one or more polarizing elements 12c, and one or more optical filters 12d, to be discussed in detail below. Imaging subsystem 14 thus also shows example components and arrangements of components, but is also not limited to such disclosed components and/or arrangements of components (also denoted as 1, 2, 3, 4). The imaging subsystem 14 in one example may include one or more array detectors 14a, a lens system 14b, one or more polarizing elements 14c, and one or more optical filters 14c, also to be discussed in detail below. Imaging subsystem 14 within system 10 also shows image enhancement electronic hardware and software 14e (i.e., a processing means), as generally illustrated via an operational block.

Turning back to FIG. 1 so as to discuss the method of embodiments herein with respect to system 10, the method involves using polarization filtering and illumination with NIR light for enhanced visualization (i.e., improved image contrast) of veins and other vascular and sub-dermal structures located below the human skin. In particular, NIR light is used for illuminating an area of interest (AOI) because it is capable of maximum photon penetration depth in tissues. In addition, the specular reflection image component is removed using polarized NIR illumination. In particular, since the specular reflection image component arises from photons that have undergone a single reflection event per detected photon, these photons maintain their polarization state. Therefore, by using polarized illumination and detecting the orthogonal image components, the specular reflection image component can be practically eliminated. In this regard, the present invention may incorporate methods for reducing or eliminating part of the signal using polarization methods and image processing via acquisition of images at different wavelengths, described in the following references: S. G. Demos and R. R. Alfano, "Optical Polarization Imaging" Applied Optics, 36, 150-155, 1997; R. R. Alfano and S. G. Demos, "Imaging of Objects Based Upon the Polarization or Depolarization of Light", U.S. Pat. No. 5,929,443; and R. R. Alfano and S. G. Demos, "Imaging of Objects Based Upon the Polarization or Depolarization of Light", U.S. Pat. No. 5,847,394, all of which are incorporated by reference herein.

The imaging system 10, as shown in FIG. 1, provides direct imaging of the AOI that is captured by a custom but more often a conventional array detector (such as CCD or CMOS or any array capable of being incorporated with the embodiments disclosed herein) and presented to the operator on a display screen such as an LCD monitor or a computer or tablet screen. In this manner, the present invention may be used, for example, for imaging of veins in a clinical setting, in a hospital, while attending to a patient in an ambulance or in a doctor's office. The present invention may also be used, without limitation, for vein visualization, imaging normal and abnormal vascular structures, vein imaging, subsurface imaging and imaging in a scattering medium.

The imaging system 10 of the present invention may include devices, components, modules or sub-systems for NIR illumination and image acquisition and processing, and may further include additional devices, components, modules or sub-systems for image recording and display. It is to be appreciated that each of the devices, components modules, or sub-systems of the present invention may be provided as a separate standalone unit of the imaging system 10, or attached to or otherwise integrated with other components of the imaging system.

Illumination Device, Component, Module, or Sub-System

In further detailing system 10 in FIG. 1, the imaging system 10 first includes an illumination system, component, module, or sub-system 12 capable of illuminating an AOI with NIR light provided by illumination elements 12a. The illumination elements 12a may include, but are not limited to, a NIR light source, such as one or more light emitting diodes (LEDs) or a NIR laser that operate in the NIR spectral range. As additional illumination light source embodiments, a conventional infrared emission source that is heated to emit a continuous band of optical radiation, e.g., an infrared igniter source element, incandescent sources filtered for NIR, and supercontinuum lasers (which emit light in the entire 400-2400 nm wavelength range), etc. can also be incorporated into the embodiments herein if desired.

Preferably however, illumination elements 12a, e.g., LEDs or a laser diode (often low power light sources), are desired based on their compact nature. The LEDs or laser diode may be designed or otherwise configured (properly modified) to provide nearly uniform illumination of the AOI during operational conditions, such as by being appropriately positioned with respect to the image acquisition component, and/or being accompanied by additional optical elements such as light diffusers that enable near uniform illumination of the AOI. Furthermore, as part of the illumination subsystem 12, an optical system is provided including one or more optical elements which control at least one of spectral and polarization properties of the NIR light, and which are positioned so that NIR light output from the light source is passed through the optical system prior to illuminating the imaged area. The optical system may include such optical elements as an illumination uniformity module 12b, polarizers 12c (broadband and/or near field polarizers), optical filter 12d (including one or more of narrow band interference filters, bandpass filters and long wave pass filters, waveplates, etc.) to control the illumination light spectral and polarization properties.

Specific aspects of the illumination light that are controlled are the spectral content of the light, the intensity and spatial distribution of the light (uniform and constant illumination of the imaged area), as well as the polarization of the illumination light. In one example embodiment, the corresponding elements of the illumination subsystem 12 may be arranged in the following order: elements for providing illumination (e.g., illumination source); elements for intensity uniformity; elements to control polarization state; and elements to isolate the above elements from the environment. It is notable that spectral filters can be positioned anywhere.

The following is additional description regarding subranges specific to different classes of people (dark/light skin; fat content, baby, low blood pressure, etc.) The illumination source uses light mostly in the NIR spectral range from about 650 nm to about 1400 nm. The illumination bandwidth can be narrow (on the order of 1 nm or less) or broader (on the order of 20 nm or more) and can be determined by specific requirements of the design such as the particular intended use and/or cost of system components. In particular, for imaging individuals with darker skin, the optical performance may be associated with illumination around 850 nm and this illumination can be relatively broad. To image individuals in which a fat layer is located between the skin and the veins (such as more obese individuals), illumination in the 700 nm or 790 nm spectral range, and within a relatively narrow band (e.g., on the order of 10 nm or less) is required to use the narrow spectral band where absorption by fat is minimal. Other case examples may require different illumination wavelengths for optimal vein visualization and imaging.

Uniform and Constant Illumination of the Imaged Area

Figure 6:
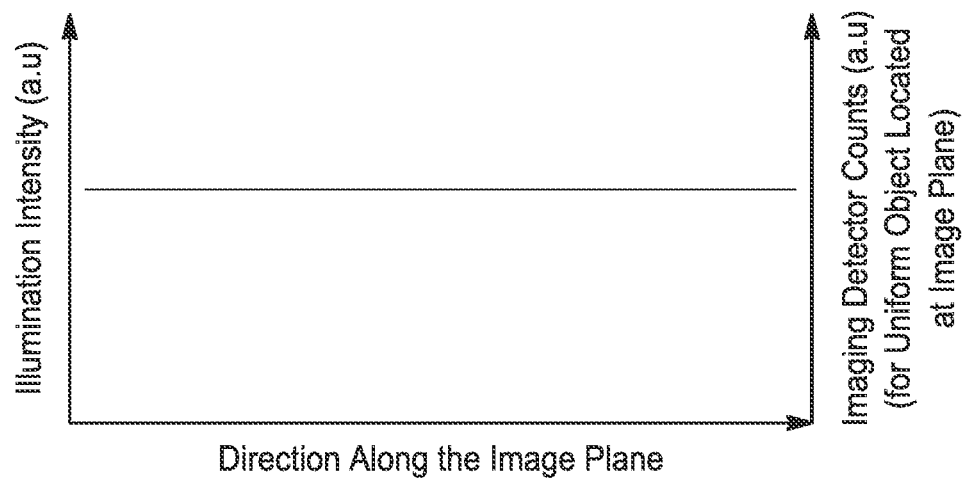
FIG. 6 shows a plot of Illumination intensity and Imaging Detector Counts versus a direction along the image plane to illustrate nearly uniform illumination of an imaged area, as disclosed herein.

Within the imaged area, there can be (and typically is) a large range of intensity recorded by the imaging device. However, in a particular location within the imaged area, the VVS (vein visualization signal) is within a small range of intensities compared to the signal obtained those portions of the imaged area that do not contain veins. To achieve a simple image enhancement method, the present invention displays only a narrow range of intensities containing the VVS, as shown in FIGS. 2 and 3. This is a simple and inexpensive method that does not require digital image processing. But for this to work, the VVS signal intensity should be similar throughout the imaged area. This requires a nearly uniform illumination of the imaged area, as defined in FIG. 6. Even with digital image processing, the uniform illumination beneficially offers better results. It is to be appreciated that as seen in FIG. 2, uniform illumination is provided directly, whereas in FIG. 3 uniform illumination is produced by post-processing, i.e., applying a correction function to correct for the non-uniformity.

The illumination uniformity module 12b may be based on (a) physical arrangement of light emitting elements or (b) redistribution of light via optical elements. In case (a), the uniformity illumination module 12b is most often positioned in position 2 of FIG. 1. In case (b), it depends on if the optical element causes depolarization of light or not. If it does not cause depolarization of light, then the illumination uniformity module 12b, the polarizing element 12c and the optical filter 12d can be placed in positions 2, 3 and 4 in FIG. 1 in any order. If the optical element causes depolarization of light, the polarizing element 12c must be positioned after the uniformity illumination module 12b while the optical filter 12d can be positioned before module 12b or element 12c, in between the module 12b and element 12c, or after the module 12b and element 12c. It is to be noted that in the above discussion, it is assumed that the optical filter 12d does not cause depolarization of the illumination light. If it does, then the polarizer 12c is often positioned after the optical filter 12d (however such filter may not be selected for a system that is based on the present invention). For the various permutations of ordering the optical components of the illumination sub-system 12, the following describes some of the criteria/requirements which make the various ordering schemes (for modules 2-4, not 1) possible. The illumination element 12a (i.e. source) is always in position 1. The polarization elements 12c and the optical filter 12d can be exchanged in position. Typically the optical filter 12d is in position 4 so this subassembly is also acting as a barrier with the environment (as the filter can be selected from a glass or other high strength material).

Imaging Device, Component, Module, or Sub-System

Although briefly described above, the imaging device, component, module, or sub-system 14 of the present system 10, in further detail also includes an image acquisition device, component, module, or sub-system 14a. As one example, this may be a digital camera system or 2-dimensional array detector, or any array camera that can be incorporated herein, e.g. as shown generally in FIG. 1, that detects a portion of the illumination light that is reflected from the AOI towards the imaging subsystem 14. The imaging subsystem 14 also incorporates a lens system 14b for imaging the AOI onto a detector array such as a CCD or CMOS device, of the image acquisition device 14a. The imaging lens may be designed to provide an in-focus image over a wide range of distances from the system so that the AOI can be correspondingly located within this range. This allows the operator to acquire images while the relative position of the device to the AOI can be changed in both the separation length and the angle with respect to the AOI surface. Furthermore, the lens 14b can provide adjustable zoom (magnification) and focus that can be selected by the operator. Thus, such operations allows a user, as example embodiments, to select in a predetermined manner a desired magnification and focus or in an automatic selectable configuration, provide for the desired magnification and focus for the image acquisition device.

Furthermore, optical modules, including one or more optical elements that often entail polarization control elements 14c and optical filters 14d, are configured to allow rejection of unwanted one or more optical components from the detected signal, and may be positioned before or after the lens system 14b in order to increase the relative intensity of the VVS compared to the total detected signal by the imaging detector 14a. Such unwanted one or more detected signal components arising from the illumination of the AOI by the systems illumination source can cause degradation of the image contrast between the veins and the surrounding tissue. In addition, these system optical elements are selected to reject or reduce one or more optical components from ambient light such as from fluorescent or white LED light sources or from Incandescent or halogen light bulb, or even from indirect light from the sun.

In this manner, the image acquisition and processing components of the imaging subsystem 14 function to detect the portion of the illumination light that is reflected towards the imaging subsystem 14 of FIG. 1, after it is passed through additional optical elements. For example, the passed through optical elements can include: optical filters 14d and polarization control elements 14c that allow rejection of unwanted optical components, such as, light components that can cause degradation of the contrast between the veins and the surrounding tissue and reject components from ambient light. Commercially available security cameras with night vision capabilities may, as example components, be selectively used for the illumination and image acquisition components based on predetermined criteria for the lens design, the LED emission wavelength, the ability for wireless video transmission, portability, etc.

It is to be appreciated that with the imaging subsystem 14, while the lens system 14b, the filter 14d and the polarizer 14c are generally exchangeable in position, some lenses may cause depolarization (or rotation of the polarization) of the propagating light. In this case the polarizer 14c is often positioned before the lens system 14b. It is to be understood however, that the filter 14d can still be positioned anywhere (positions 2-4) within the imaging subsystem 14 assuming that it does not change the polarization state of the light.

The imaging subsystem 14 of the system 10 of the present invention may also include an image-processing device, component, module, or sub-system that is designed to provide contrast enhancement of the veins via either electronic components or via digital image processing means to further enhance the visualization of the veins. This may be implemented using additional signal electronics and/or software 14e. The additional electronics and/or software may be provided for post-processing the detected signal to further enhance image contrast. This may involve various means including the mathematical processing of the image or the selection for display of only a range of intensities within the dynamic range of the imaging device. Such image processing can be provided via electronic or hardware (e.g., a toggle switch) components located on the imaging and/or display system or can be attained via computer software, as to be discussed in further detail below.

Figure 4A:
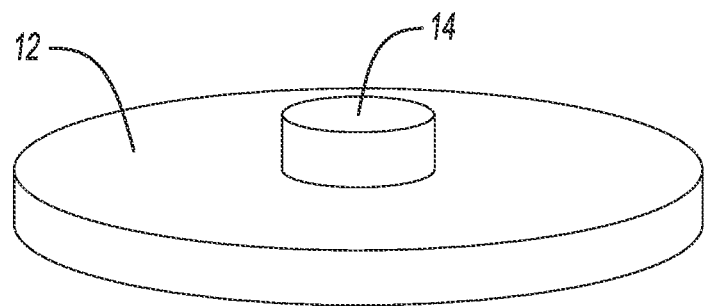
FIG. 4A illustrates relative positions of the imaging subsystem and the illumination subsystem of the present invention in accordance with an example embodiment.
Figure 4B:
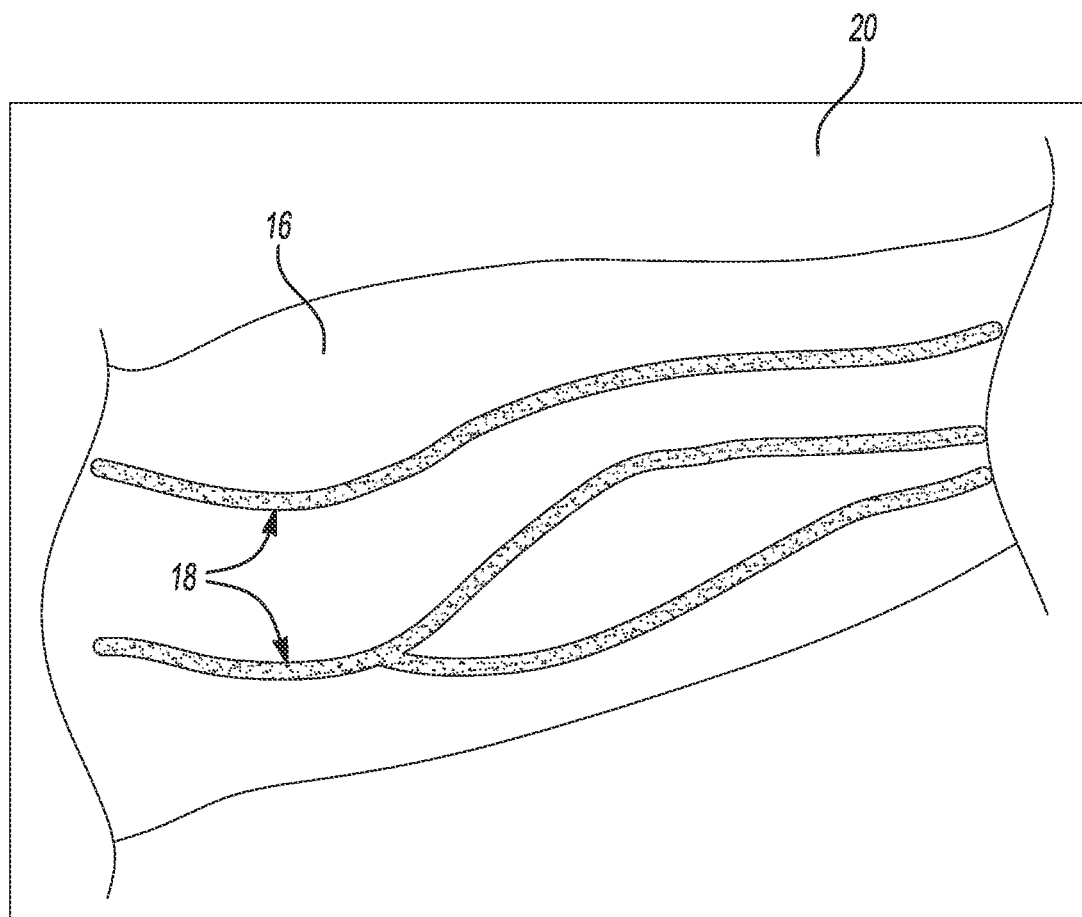
FIG. 4B illustrates an imaged area of interest (AOI) using an example embodiment, as disclosed herein.
Figure 5A:
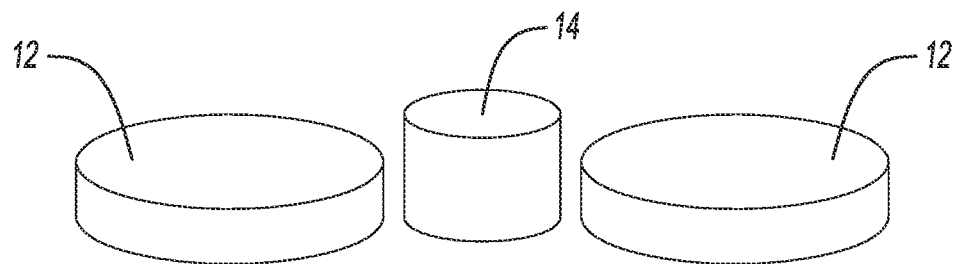
FIG. 5A illustrates another example embodiment where two illumination subsystems are used to illuminate an imaging area.
Figure 5B:
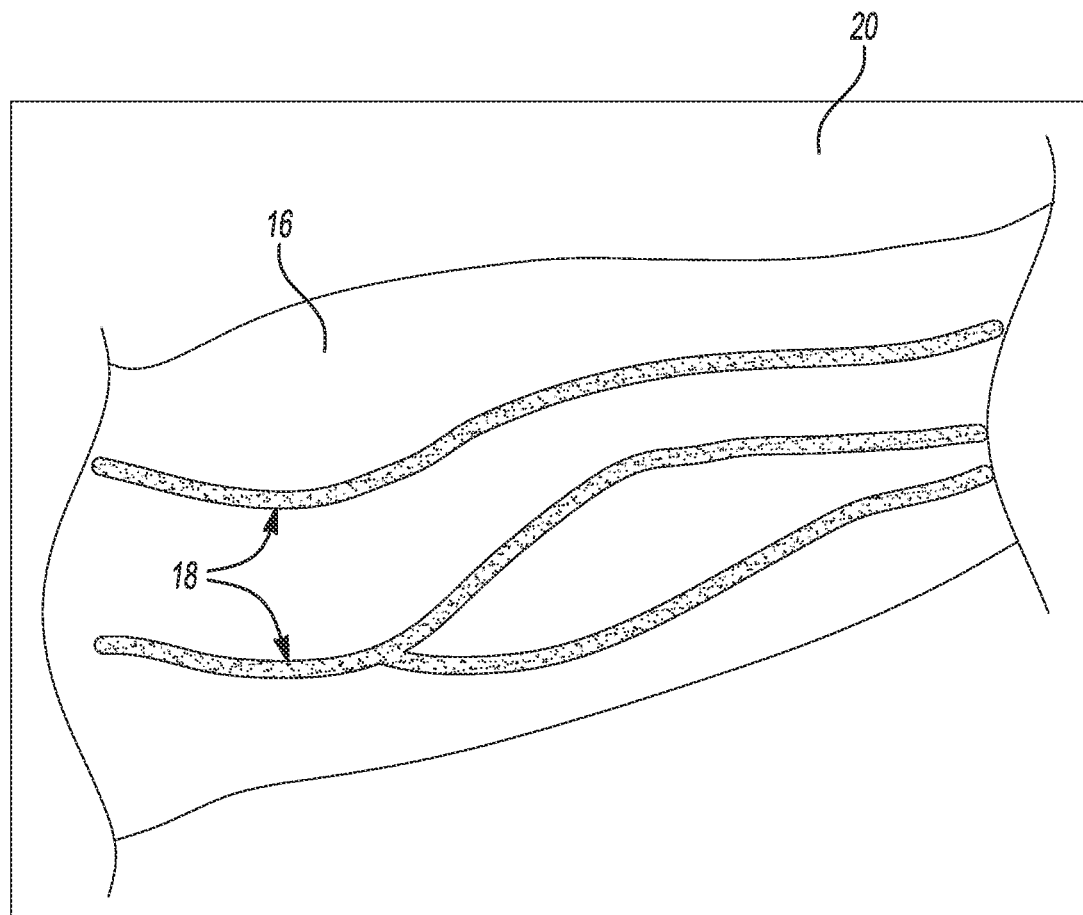
FIG. 5B illustrates an imaged area of interest (AOI) using the second example embodiment, as shown in FIG. 5A.

Various aspects of the signal collection light for image formation may be controlled including spectral content of the light and the polarization of the signal light. The polarization of the signal light must be the orthogonal polarization state from the illumination polarization state (which can be linear, circular, elliptical, etc.). Furthermore, FIG. 4A shows an example general configuration wherein the imaging subsystem 14 and the illumination subsystem 12 may be coupled in a close arrangement (e.g., coupled together, even co-linearly). FIG. 5A shows an additional general example configuration wherein the imaging subsystem 14 and the illumination subsystem 12 can be decoupled. It is also to be appreciated that FIG. 5A also shows, for example, a non-limiting embodiment wherein two illumination subsystems 12 are being used to illuminate an imaging area. It is also to be noted that while the components (e.g., Illumination subsystem 12 and imaging subsystem 14) are depicted with circular geometries in the examples, the components can also be configured in other geometric component styles, such as, rectangular, square, elliptical, etc., where warranted to provide the working embodiments of the present invention. The reader is also to note that FIG. 4B and FIG. 5B illustrate example imaged areas (i.e., imaging area 20) of an arm 16 and its vein structure 18, via the example embodiments generally shown in FIG. 5A and FIG. 5A.

Image Display Device, Component, Module, or Sub-System

As previously discussed, within a given area of interest being imaged, there can be (and typically is) a large range of intensity recorded by the imaging device 14a. However, in a particular location within the imaged area, the VVS will fall within a small range of intensity compared to the signal from the imaged area that does not contain veins. To achieve a simple image enhancement method, the system 10 of the present invention displays only a narrow range of intensities containing the VVS, as shown in FIG. 2 and FIG. 3. This is a simple and inexpensive method that does not require digital image processing. The imaging subsystem 14 of the present invention may additionally include a monitor or other display system for graphically displaying the image within the small range of intensities. While the image has no color information (monochrome), it may be displayed in gray scale or in a color. It is to be appreciated that the display may be attached to other components of the imaging subsystem 14 or it may be separated as a standalone component of the imaging system.

Use of Fiducial Marks/Elements to Enhance Spatial Correlation

Figure 7:
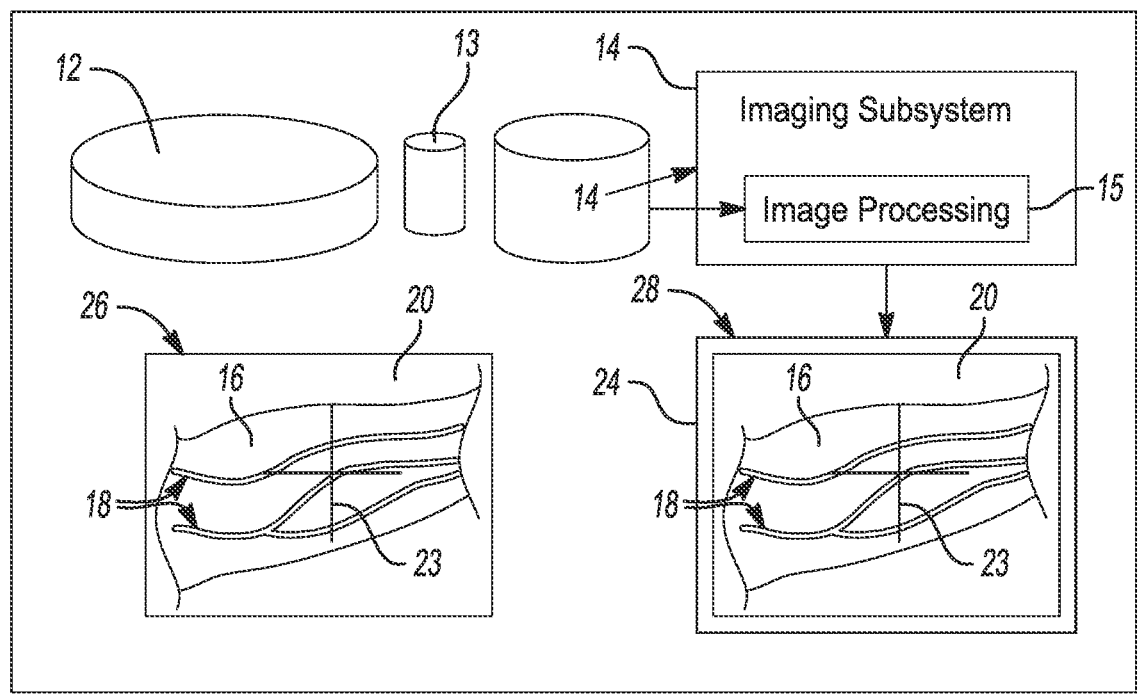
FIG. 7 shows an example projection system for co-registration.

FIG. 7 shows an example co-registration illumination system 700 to include subsystem 12, imaging subsystem 14, and image processing 15 means of captured imaged areas 20 (i.e., of an arm's 16 desired vein structure 18). The operator can visualize the vein 18 structure via some kind of a monitor 24 screen, as known to those skilled in the art, either attached or detached from the imaging subsystem 14. The co-registration itself is enabled via a projection subsystem 13 for marker location of an area. In particular, to enhance the ability of the operator to correlate the image to the visual perception, specific markers (i.e., crosshairs 23, as shown in FIG. 7) on the arm 16, veins 18, can be used that are projected on the imaged area 20, as shown in the left lower depiction 26 of FIG. 7 and displayed on the monitor 24 (or correlated to a specific location within the image presented in the monitor, such as the center of the image), as shown in the right lower depiction 28 of FIG. 7. This can include, but is not limited to, low power laser sources such as one or more red laser pointer(s) that help establish this correlation. Specific examples of methods that may be used to display displaying the cross-hairs in the example embodiments herein may involve, without limitation, a mask on CCD, or using a laser pointer which is detected by the imaging subsystem 14.

First, so as to provide further detail, fiducial marks, such a cross-hairs 23 or one or more bright spots, can be used to allow the user to associate the visual perception with the images obtained by the system 10. This is necessitated by the fact that the vein structure observed in the image obtained by the system 10 may be difficult to associate with the naked eye view of the target area (such as an arm). Using fiducial marks which are projected onto the target area, that are also highlighted in the image obtained by the system 10, beneficially assists the operator to locate the area in the arm that correlates to a specific location of interest in the image. This co-registration of the projected in the target area fiducials with the corresponding markings in the display can be achieved using two general approaches.

Second, the image display fiducials may be generated during the imaging processing step 15, as shown in projection system 700 of FIG. 7, which is after the image was recorded and transmitted. This can be achieved either by digitally processing the image to enter the fiducial markings or even by producing a marking on the display, such as the center point of the image, using simpler physical methods.

Third, the fiducial may be embedded during the image acquisition process. There are various methods for achieving this. One of the simplest methods is using the projected light on the target area to form the fiducials, which contain spectral components that can be recorded by the imaging device. This enables direct visualization of the position of the fiducials during image display. Another method involves inducing the fiducials on the array detector 14a, as general depicted in FIG. 1, which is capturing the image. This can be achieved by de-activating a number of pixels to form dark points (generating dark spots or dark lines) or by using a mask in front of the detector 14a that reduces or obstructs the collected signal to form the fiducials on the display.

The visualization embodiments described above offers enhanced visualization of structures located below the dermis, such as veins located 1 mm up to 1 cm (or more) below the skin in humans. As the visual perception of the human eye is based on the interaction of light with tissue in the visible spectral range, the features observed in the sub-dermal structure visualization embodiments described above are largely not visible by the naked eye. It is also possible that certain features that are visible by the naked eye are not visible by the sub-dermal structure visualization system. It may therefore be beneficial to devise methods that can provide both types of images to the operator. Specifically, a beneficial integrated system may contain the capability of substantially simultaneously acquiring (recording) conventional color images in combination (if desired) with the sub-dermal structure visualization images. The following discussion provides insight as to the enablement of such methods in technically realistic and cost effective designs.

Figure 8A:
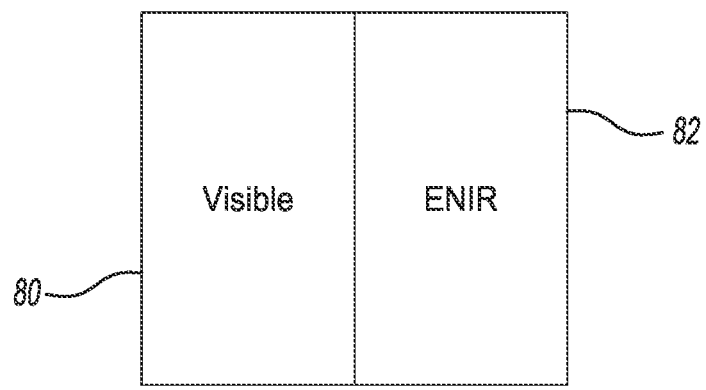
FIG. 8A shows a general depiction of an example system that requires that the visible images and enhanced near infrared images (ENIR) are captured substantially simultaneously.
Figure 8B:
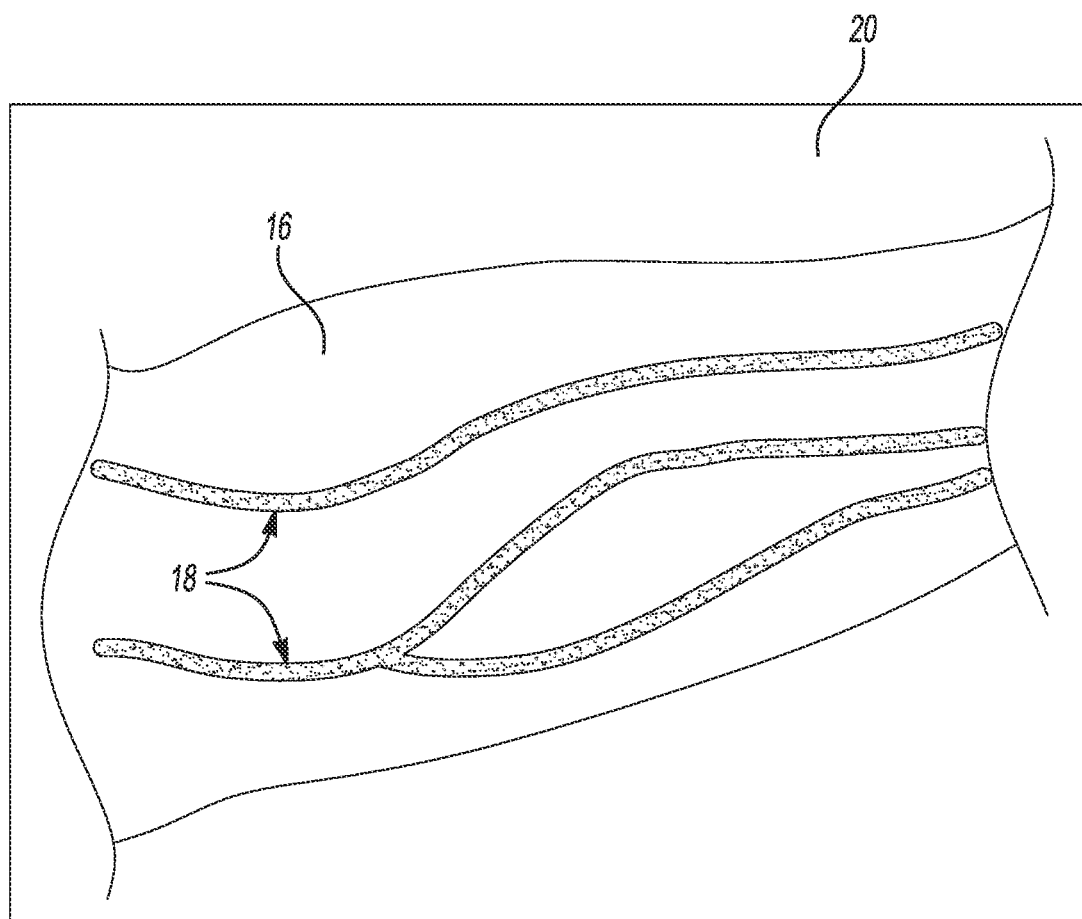
FIG. 8B illustrates an imaged area of interest (AOI) using the example embodiment, as shown in FIG. 8A.

FIG. 8A generally shows the approach which requires that both, the visible image 80 and the enhanced near infrared (ENIR) image 82 (acquired using the methods described above) are acquired "substantially simultaneously." FIG. 8B again shows the capability of an image of the arm 15 and veins 18 within an imaging area 20. It is to be appreciated that the term "substantially simultaneously" as defined herein, refers to the acquisition of images of each type in a rate that is fast enough to be perceived by a human operator as continuous (on the order of 10 frames per second) or quasi-continuous (on the order of 1 frame per second). These images can be provided to the user/operator via the following possible basic methods and/or combinations of these basic methods:

a) There are two separate sensors that work independently to acquire (record) each image type;
b) The same sensor acquires sequentially each type of image;
c) The same sensor acquires simultaneously both image types.

It must be noted that the term "sensor" refers to an integrated imaging device which can be comprised of: a) a single two dimensional detector (such as a monochrome CCD sensor), b) a coherent array of monochrome detectors recording images at different spectral ranges (such as three-CCD camera which uses three separate CCDs, each one taking a separate measurement of the primary colors, red, green, and blue), c) a single two dimensional detector containing different types of pixels designed to record different parts of the optical spectrum (such as in color sensors where different groups of pixels record the three primary colors, red, green and blue) or d) a specialty sensor designed to acquire multi-spectral images.

Furthermore, upon acquisition of each image type, each image type can be, using hardware and software apparatus for example, displayed separately in different monitors or other type of display device or the two image types can be fused together in a single image that displays in an effective manner the information contained in both images. For the more accurate co-registration of both images during the image fusion process or for seamless simultaneous display, the use of a single optical imaging element (imaging lens) to relay the image of the object to the imaging sensor(s) may be the most effective method (although not the only method). It is also to be appreciated that a particular sensor is often configured (i.e., associated/coupled) with a desired filter designed for spectral selection and purification (e.g., select and/or eliminate undesired optical components). Moreover, the desired filter(s) can be alternately configured for visible light or ENIR optical components and also alternately positioned in front of a desired filter. In addition the same sensor (i.e., the particular sensor) can also be configured optically to collect simultaneously the visible or the ENIR image components to provide an image that contains both image components.

Figure 9A:
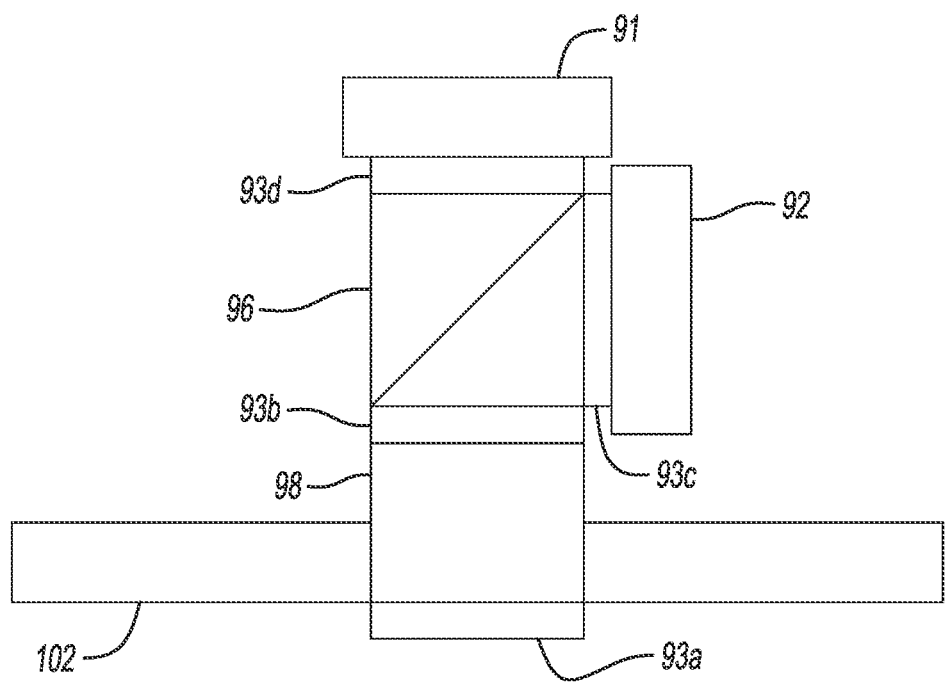
FIG. 9A shows an exemplary illumination subsystem generally indicating where various optical elements (OLs) may be positioned in a two imaging sensor configuration.
Figure 9B:
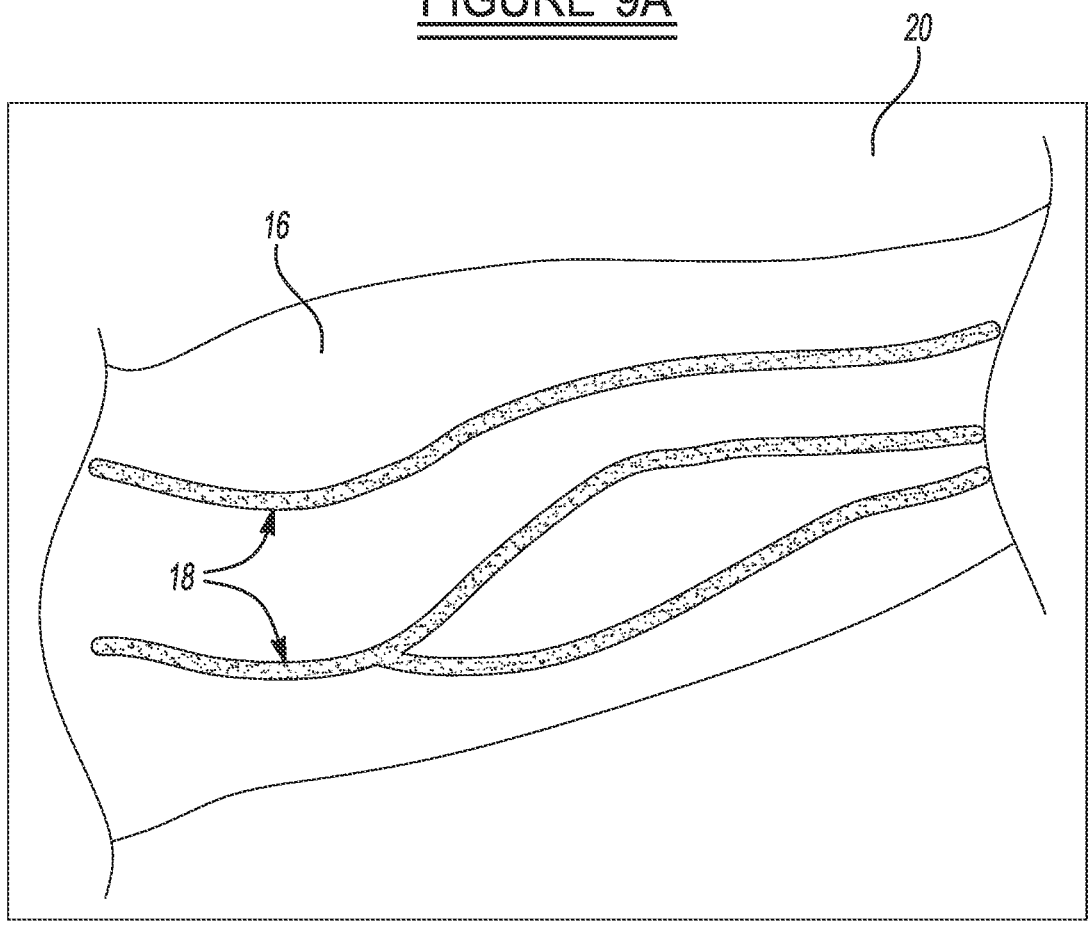
FIG. 9B illustrates an imaged area of interest (AOI) using the example embodiment, as shown in FIG. 9A.

The following discussion provides for example technical solutions in the context of the sub-dermal structure visualization methods described for the present embodiments. In particular, FIG. 9A shows an exemplary illumination subsystem which, as described before, contains illumination elements (such as LEDs), an illumination uniformity module (which can be integrated in the illumination elements), a polarizing element and optical filters. FIG. 9B again shows the capability of an image of the arm 15 and veins 18 within an imaging area 20. In detail, FIG. 9A shows at least two imaging sensors 91, 92, optical elements (e.g., modules) 93a, 93b, 93c, and 93d, a beam splitter 96, a lens system 98 and the illumination subsystem 102. The illumination elements may include specific elements that provide illumination in the visible spectrum to compliment the elements providing illumination in the NIR spectral region used for sub-dermal imaging and aid ambient visible light. The optical filter may not be used but the polarizing elements may be used as they can enhance the quality of both types of recorded images. The visible light illumination elements are not required (but they can be used to enhance the visible image) as the ambient visible light can be used for the illumination of the target area.

FIG. 9A also shows example locations where various optical elements (OLs) may be positioned. These can include, for example, a polarizer (with its polarization orthogonal to the polarization state of the illumination) and optical filters that select and/or further purify the spectral content of the collected by the lens system light to be used for image formation by each sensor. For example, such filters should allow the visible light reach the sensor used to record the visible image but eliminate the NIR light.

The system shown in FIG. 9A can also be used in a mode that allows subtraction of the background light reaching the sensors. This background light includes all light that does not originate from the illumination elements of the illumination subsystem (such as the ambient light). One simple non-limiting method (but not the only one) to execute such a task is to consecutively acquire two images by one (e.g., sensor 91) or both sensors (e.g., sensor 91 and sensor 92) when the illumination elements are turned on and when the illumination elements are turned off. The second image contains image arising from ambient light while the first image contains image arising from both, the ambient light and the light originating from the illumination elements. Subtraction (or other suitable processing) of the two images can effectively remove the image component arising from the ambient light (which will be equal in intensity in both recorded images) and provide an image arising only from the exposure of the target area to the light of the illumination elements.

Figure 10A:
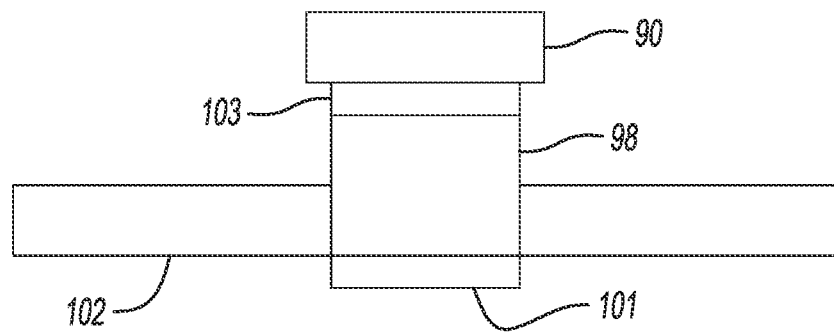
FIG. 10A shows an exemplary illumination subsystem in a one imaging sensor configuration.
Figure 10B:
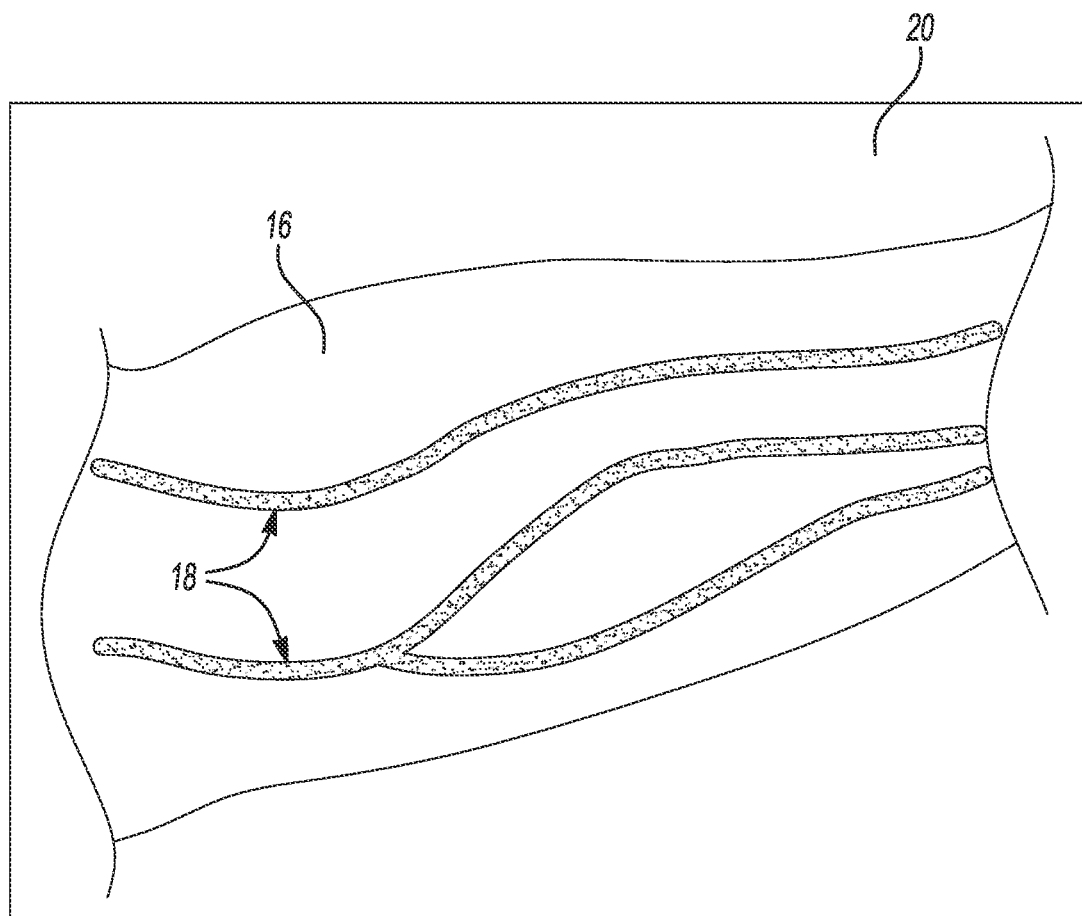
FIG. 10B illustrates an imaged area of interest (AOI) using the example embodiment, as shown in FIG. 10A.

FIG. 10A provides a schematic layout of the system that utilizes, in this example mode, one imaging sensor 90, optical elements (e.g., modules) for the acquisition of the conventional visible (color) images and the acquisition of the ENIR sub-dermal images. FIG. 10B once again shows the capability of an image of the arm 15 and veins 18 within an imaging area 20. Such a sensor 90, as shown in FIG. 10A is designed to separate and record in different sets of pixels the different spectral components of the visible light such as the red, blue and green (RGB) components used for color image recording (video recording or in color photography) in the electronics industry. In addition, this sensor should be able to record the near infrared image of the sub-dermal structures. It is well known that currently available color sensor (such as CCD and CMOS color image sensors) are also sensitive and capable of recording light in the NIR spectra region and most commonly in the 800-900 nm spectral region. For this reason, these sensors are equipped with a NIR blocking filter when used in conventional color video or photography applications to allow only the visible light reach the detector. However, by removing this filter, a conventional color image sensor can also detect the NIR light. We take advantage of this feature in this invention to enable acquisition of both, the visible and the ENIR images.

As similar to the embodiment shown in FIG. 9A, an exchangeable filter set may be used in the embodiment of FIG. 10A to allow the sensor to record either:
  a) the visible color image by placing a filter in front of the sensor that eliminates the NIR light and transmits the visible light;
  b) the ENIR image by placing a filter in front of the sensor that eliminates the visible light and transmits the NIR light;

In contrast to the design depicted in FIG. 9A, the two images are not recorded independently in the design depicted in FIG. 10A as in each instance, either the color or the NIR image are recorded or the sum of the color and NIR image components. As a result, the image can be displayed as following:
  a) The operator can select which image to be displayed;
  b) Each image is alternately (up to a desired video rate) displayed on the same monitor;
  c) Alternately display the two images in two different monitors (with additional hardware and/or software to separate the two images);
  d) The image acquisition and display can be very fast, up to a desired video rate, so the alternate acquisition may not be perceived by the operator to whom it will appear as viewing two separate images at video rate;
  e) Can be fused in to a single pseudo-color image containing both image components.

In the embodiment of FIG. 10A, a proper filter may be used (such as a filter that allows the visible and part of the NIR spectrum to pass and reach the sensor) to allow the sensor to simultaneously record and form images using both, the visible and ENIR components. As mentioned earlier, currently available color sensor are also sensitive and capable of recording light in the NIR spectra region and most commonly in the 800-900 nm spectral region. By removing the NIR light blocking filter, a conventional color image sensor can also detect the visible and NIR light in the about 800-900 nm spectral range. In addition, the pixel used to record the red color are also able to record the NIR light up to about 900 nm. Therefore, one can devise various methods to simultaneously record the visible and ENIR components in a conventional color imaging sensor. This approach also fuses the Visible and the ENIR image components. The resulting image appears to be "color" but also contains the ENIR component. Such method in various specific implementations can be used to provide enhanced visualization of the veins while the color image components are also visible and presented to the user.

FIG. 10A also shows a system to include the illumination subsystem 102, all of which is substantially identical to that described in FIG. 9A containing, for example, illumination elements (such as LEDs), a illumination uniformity module, a polarizing element and an optical filter. The illumination elements may include specific elements that provide illumination in the visible spectrum in addition to the elements providing illumination in the NIR spectral region used for sub-dermal imaging. The optical filter may not be used but the polarizing elements may be used as they can enhance the quality of both types of recorded images. The visible light illumination elements are not required (but they can be used to enhance the visible image) as the ambient visible light can be used for the illumination of the target area.

FIG. 10A also shows the incorporation of various optical elements (OLs). These include a polarizer 101 (with its polarization orthogonal to the polarization state of the illumination) and optical filters 103 that select and/or further purify the spectral content of the collected light by the lens imaging system. The order of the location of one or more optical elements (OLs) 101, 103, lens system 98, and exchangeable filter set (not specifically detailed) is not fixed and any of these elements can be positioned in front of the other as needed by the specific design.

The system shown in FIG. 10A can also be used in a mode that allows subtraction of the background light reaching the sensors using methods similar to those described for the design depicted in FIG. 9A. This background light includes all light that does not originate from the illumination elements of the illumination subsystem. One simple method (but not the only one) to execute such task is to consecutively acquire two images while the illumination elements are turned on and when the illumination elements are turned off. The second image arises from ambient light while the first image contains image arising from both, the ambient light and the light originating from the illumination elements. Subtraction (or other suitable processing) of the two images can effectively remove the image component arising from the ambient light and provide an image arising only from the illumination elements that will be of higher quality. This method of background subtraction can be used when the sensor operates in the visible image mode, the ENIR imaging mode or in the fused image mode as described above.

Image Display

The image display unit can be attached or detached from the illumination subsystem and/or imaging subsystem. The image acquisition, processing and display should be fast enough to be perceived by a human operator as continuous (on the order of 10 frames per second or higher) or quasi-continuous (on the order of 1 frame per second). The display module should have the following characteristics:
  a) The image display area is within a range that the operator can comfortably view the vein structures in the arm. Although this may vary with the operator and working environment, a specific example may be a monitor having diagonal dimension between about 7 and 10 inches when the viewing operator is located up to 100 cm to 150 cm from the monitor.
  b) The image display has pixel resolution that matches or exceeds the pixel resolution of the image as provided by the sensor.
  c) The image display has an aspect ratio that matches the aspect ratio of the image provided by the sensor.
  d) The image display has a sufficiently high Luminance and Contrast Ratio that can support or enhance the image contrast provided by the image enhancement module.

Communications and Data Storage Device, Components, etc.

The imaging subsystem 14, as shown in FIG. 1 of the present invention, may additionally include a communication component for transmitting the image to the display. This can be achieved, for example, with wired or wireless communication means, as discussed in detail below. The image can be stored in computer memory or other types of storage media (discussed below) in the form of still images or a sequence of images (such as movies). The transmission and recording system can include recording of images and ambient sound or it can incorporate two-way sound between the display and the imaging devices. The latter is applicable when the display (or an additional display reproducing the image of the first display) is in a remote location (as further detailed below) so that instructions from the observer of the second display can be transmitted to the operator of the imaging device.

Even more particular, the operation of the enhancement software 14e in addition to operation of the system 10 and components therein system 10, as shown generally in FIG. 1, can be controlled and respective data can be acquired by a control and data system (not depicted) of various circuitry of a known type, which may be implemented as any one or a combination of general or special-purpose processors (digital signal processor (DSP)), firmware, software to provide instrument control and data analysis for the system 10. This also includes the aforementioned enhancement software 14e, and/or related instruments, and hardware circuitry configured to execute a set of instructions that embody the prescribed system 10, data analysis and control routines of the present invention.

It is also to be appreciated that instructions to activate or deactivate the embodiments herein, and/or the exporting/displaying/outputting the instruments characteristics, etc., may be executed via a data processing based system (e.g., a controller, a computer, a personal computer, a handheld device, etc.), which includes hardware and software logic for performing the instructions and control functions.

In addition, such control functions can also be implemented as provided by a machine-readable medium (e.g., a computer readable medium). A computer-readable medium, in accordance with aspects of the present invention, refers to non-transitory media known and understood by those of ordinary skill in the art, which have encoded information provided in a form that can be read (i.e., scanned/sensed) by a machine/computer and interpreted by the machine's/computer's hardware and/or software.

System 10 shown in FIG. 1 also can be configured with a communication interface to include a wireless (as briefly discussed above) transmitter/receiver unit that is configured to transmit signals from a processor to other devices, and to receive signals from other devices. For example, the communication interface permits a processor to communicate with other devices via a wireless network that includes multiple devices connected to the network, and/or via a direct connection to another device. Such a configuration can enable the system 10 to communicate with a central computer system to update the database of reference information stored in a storage unit. In addition, the processor can also, if desired, contact the central computer system to receive updated reference information about, as one example, a particular patient, and such a configured processor can also receive automatic updates that are delivered by the central computer system.

In some embodiments, system 10 can be connected to other devices over other types of networks, including isolated local area networks and/or cellular telephone networks. The connection can also be a wireless connection or a physical coupling.

As non-limiting examples of a wireless connection, such an arrangement can include commercial wireless interfaces, such as but not limited to, radio waves (WiFi), infrared (IrDA), or microwave technologies that also allow integration into available portable personal devices, such as, but not limited to, cell phones, pagers, personal identification cards, laptops, etc.

The wireless network can, for example, be configured with Bluetooth, which operates in a globally available frequency band (i.e., 2.4 GHz), ensuring communication compatibility worldwide, or Electronic and Electrical Engineers IEEE technologies (e.g., IEEE) 802.11a or IEEE 802.11b) as the communication means based on its present common use in both business and home environments. Moreover, other protocols for wireless, such as IEEE 802.15, IEEE 802.16, GPS, 3G and others, may also be configured as a protocol for the communication standard of the present embodiments disclosed herein.

With respect to physical wired coupling, the coupling can be by way of a dedicated coupling I/O means, such as a USB port (not shown) to provide, for example, (feedback) via the embedded software (e.g., firmware) or instructions received from processor for programmatic control instruction.

In addition, the system 10, as shown in FIG. 1, can include a control panel, such as a graphical user interface (GUI) that enables a system operator to set configuration options and change operating parameters. In some embodiments, system 10 can also include an internet-based configuration interface that enables remote adjustment of configuration options and operating parameters. The interface can be accessible via a web browser, for example, over a secured or insecure network connection. The internet-based configuration interface permits remote updating of system 10 by a central computer system or another device.

As a beneficial aspect of the present application, a coupled processor (not shown) can also send, if desired, an electronic signal to a system operator to provide a warning message should a procedure, such as, for example, when an invasive medical procedure becomes perilous while using system 10, as shown in FIG. 1, as a visualization aid in the procedure. The processor can also be configured to sound an audio alarm via a speaker to alert the system operator.

Although the description above contains many details and specifics, these should not be construed as limiting the scope of the invention but as merely providing illustrations of some of the presently preferred embodiments of this invention. Other implementations, enhancements and variations can be made based on what is described and illustrated in this patent document. The features of the embodiments described herein may be combined in all possible combinations of methods, apparatus, modules, systems, and computer program products. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

I claim:

1. A method for visualizing a sub-dermal structure, the method comprising:

illuminating an imaged area of interest (AOI) including sub-dermal regions thereof with near-infrared (NIR) light that is passed through a first optical system for controlling at least one of spectral and polarization properties of the NIR light prior to illuminating the imaged area of interest, and wherein the NIR light provides both a uniform and a constant illumination over the imaged area of interest, and the imaged area of interest is substantially larger than a vein and stationary;

using a filter to reject an unwanted one or more optical components of an optical signal reflected back from the imaged area of interest, while passing one or more desired optical components of the optical signal reflected back from the imaged area of interest, while illuminating an entirety of the imaged area of interest (AOI) with the NIR light having the uniform and constant illumination, wherein the one or more desired optical components represent specific portions of the sub-dermal regions where specific anatomical structure of interest is present;

wherein the one or more desired optical components of the reflected optical signal comprise a vein visualization signal representing only a portion thereof that falls within a sub-range of intensities, relative to intensities of a remainder of the reflected optical signal which has been passed by the filter, to assist in visualizing a vascular structure below a skin layer of a patient;

while continuing to project the NIR light having the uniform and constant intensity, using an image enhancing subsystem to select for display only the subrange of the intensities of the desired optical components having been passed by the filter, and to reject intensities pertaining to non-vascular structure, so that the sub-range of the intensities selected for display represent only the vein visualization signal; and while continuing to project the NIR light have the uniform and constant intensity, displaying the vein visualization signal to generate a display of the vascular structure on a display system.

2. The method of claim 1, wherein illuminating the imaged area of interest (AOI) comprises using a stationary light source to illuminate the imaged area of interest.

3. The method of claim 1, wherein the using an imaging system having an optical filter comprising using at least one of:
an optical polarizer; or
one or more waveplates.

4. The method of claim 1, wherein illuminating the area of interest (AOI) with NIR light further comprises controlling a spectral content of the NIR light.

5. The method of claim 1, wherein illuminating the area of interest (AOI) with NIR light further comprises controlling an intensity spatial distribution of the NIR light.

6. The method of claim 1, wherein illuminating the area of interest (AOI) with NIR light further comprises controlling a polarization of the NIR light.

7. The method of claim 1, wherein the NIR light is selected to have a specific wavelength based on considerations of at least one of skin color and a degree of body fat layer of an individual.

8. The method of claim 1, illuminating the area of interest (AOI) with NIR light comprises using a wavelength for the NIR light between 650 nm to 1400 nm.

9. The method of claim 1, further comprising illuminating the area of interest (AOI) with at least one additional illumination signal which provides visible illumination of the AOI along with existing ambient visible light.

10. The method of claim 1, further comprising using a processor to subtract spectral components resulting from ambient light by creating an additional image, which is recorded while no NIR illumination is being provided, from the image obtained with using the NIR illumination.

11. The method of claim 1, wherein the imaging subsystem only passes portions of the reflected optical signal having one or more desired spectral or polarization properties, and wherein the one portions of the reflected optical signal passed represented the desired one or more optical components.

12. The method of claim 11, further comprising using the passed one or more desired optical components to generate an image intensity histogram containing the vein visualization signal representing the vein.

13. The method of claim 12, wherein the imaging subsystem uses a two dimensional array detector configured to collect the reflected optical signal.

14. The method of claim 1, further comprising also transposing image display fiducials from the image area on the display system along with the vascular structure represented by the vein visualization signal, to enhance spatial correlation of the vascular structure with other anatomical features falling within the area of interest (AOI).

15. The method of claim 14, further comprising alternately displaying the image display fiducials and the vein visualization signal on the display system.

16. A method for visualizing a sub-dermal structure, the method comprising:

illuminating an imaged area of interest (AOI) including sub-dermal regions thereof with near-infrared (NIR) light that is passed through a first optical system for controlling at least one of spectral and polarization properties of the NIR light prior to illuminating the imaged area of interest, and wherein the NIR light provides both a uniform and a constant illumination over the imaged area of interest, and the imaged area of interest is substantially larger than a vein and stationary;

the NIR light further selected to have a specific wavelength based on considerations of at least one of skin color and a degree of body fat layer of an individual;

while illuminating the imaged area of interest with the NIR light, using a filter to reject an unwanted one or more optical components of an optical signal reflected back from the imaged area of interest, while passing one or more desired optical components of the optical signal reflected back from the imaged area of interest which have one or more desired spectral or polarization properties, while illuminating an entirety of the imaged area of interest (AOI) with the NIR light having the uniform and constant illumination, wherein the one or more desired optical components a detected one or more desired optical components, and represent specific portions of the sub-dermal regions where specific anatomical structure of interest is present, and where the imaged area of interest (AOI) is substantially larger than the sub-dermal regions having the specific anatomical of interest;

while illuminating the imaged area of interest with the NIR light, using the detected one or more desired optical components to produce an image intensity histogram;

while illuminating the imaged area of interest with the NIR light, analyzing the image intensity histogram and selecting therefrom only a selected sub-range of intensities present in the histogram to form a subportion of the detected one or more desired optical components whose intensities correspond only to vascular structure, wherein the selected sub-range of intensities comprise a vein visualization signal, to assist in visualizing the vascular structure below a skin layer of a patient; and while illuminating the imaged area of interest with the NIR light, using the vein visualization signal to generate a display of the vascular structure on a display system.

17. The method of claim 16, wherein the illuminating an imaged area of interest (AOI) is carried out using a constant illumination NIR light source.

18. A method for visualizing a sub-dermal structure, the method comprising:

illuminating an imaged area of interest (AOI) including sub-dermal regions thereof with near-infrared (NIR) light, wherein the NIR light provides both a uniform and a constant illumination over the imaged area of interest, and the imaged area of interest is substantially larger than a vein and stationary, and wherein the NIR light comprises a wavelength for the NIR light between 650 nm to 1400 nm;

controlling spectral and polarization properties of the NIR light prior to the NIR light illuminating the imaged area of interest;

while continuing to illuminate the imaged area of interest with the NIR light having the uniform and constant illumination, using an optical filter to reject an unwanted one or more components of an optical signal reflected back from the imaged area of interest, while passing a desired one or more components of the optical signal being reflected back which has one or more desired spectral and polarization properties, while continuously illuminating an entirety of the imaged area of interest with the uniform and constant illumination;

while illuminating the area of interest using the NIR light having the uniform and constant illumination, detecting the one or more desired optical components of the optical signal reflected back from the imaged area of interest, wherein the one or more optical components represent specific portions of the sub-dermal regions where specific anatomical structure of interest is present;

creating a histogram using the one or more desired optical components;

while illuminating the area of interest using the NIR light having the uniform and constant illumination, using an image enhancing subsystem to analyze the histogram and to select therefrom only a sub-range of intensities present in the histogram, the sub-range of intensities corresponding only to vascular structure and representing a vein visualization signal, the vein visualization signal representing the specific anatomical structure of interest; and while illuminating the area of interest using the NIR light having the uniform and constant illumination, displaying the vein visualization signal on a display system as an image in accordance with at least one of a selected aspect ratio, a desired resolution and an image contrast that enhances the image.

* * * * *